United States Patent [19]

Demachi

[11] Patent Number: 5,367,912
[45] Date of Patent: Nov. 29, 1994

[54] APPARATUS FOR ANALYZING LIQUID SPECIMEN

[75] Inventor: Takashi Demachi, Kobe, Japan

[73] Assignee: Toa Medical Electronics Co., Ltd., Kobe, Japan

[21] Appl. No.: 969,573

[22] Filed: Oct. 30, 1992

[30] Foreign Application Priority Data

Nov. 20, 1991 [JP] Japan .................................. 3-331284

[51] Int. Cl.$^5$ ............................................. B01L 11/00
[52] U.S. Cl. .................................................. 73/863.73
[58] Field of Search ........... 73/863.73, 864.83, 864.84; 422/82-82.13, 67, 103

[56] References Cited

U.S. PATENT DOCUMENTS

| | | | |
|---|---|---|---|
| 3,764,268 | 10/1973 | Kosowsky et al. | 422/88 |
| 3,909,203 | 9/1975 | Young et al. | 422/67 |
| 4,729,876 | 3/1988 | Hennessy et al. | 73/863.73 |

Primary Examiner—Robert Raevis
Attorney, Agent, or Firm—Jones, Tullar & Cooper

[57] ABSTRACT

An apparatus for analyzing liquid specimen comprising a sampling valve (11) consisting of two fixed elements (10), (14), and a movable element (12) held between these fixed elements, sample aspiration means (C0), diluent liquid dispensing means (Ci), and chamber (Bi) for receiving diluent liquid and sample, which further comprises measuring item setting means (30), control means (28) for selectively operating the dispensing means, and driving means (26) for driving each dispensing means according to its control signal. By composing in this manner, in the apparatus for analyzing liquid specimen for aspirating and pushing liquid specimen such as blood in cylindrical shape by means of a sampling valve, taking out quantitatively, treating as required, and analyzing, only a sample necessary for measurement is selected, and is diluted or otherwise treated.

6 Claims, 6 Drawing Sheets

APPARATUS FOR ANALYZING LIQUID SPECIMEN

BACKGROUND OF THE INVENTION

The present invention relates to an apparatus for analyzing a liquid specimen such as blood. The apparatus has a sampling valve for aspirating and pushing the liquid specimen (sample) in cylindrical shape, removing it quantitatively, and treating and analyzing it as required, and more particularly to an apparatus for analyzing liquid specimen applicable to discrete tests capable of selecting only a specimen necessary for measurement (examination), and treatment by diluting or the like.

An apparatus for counting blood corpuscles such as erythrocytes, an apparatus for classifying leukocytes, and an apparatus for counting reticulocytes are well known. An apparatus combining these plural functions into one (multifunctional apparatus) is also known. In such multifunctional apparatus, results of measurements (examination) of multiple items can be obtained by a single sampling operation. Depending on the specimens, however, unnecessary items may be also measured, which means waste of sample and reagent.

To eliminate such waste, it is required to have a function for sampling only the necessary portion in each specimen, and taking into the apparatus for analysis (discrete test function). For example, in the field of biochemical examination, it depends on the sampling system in which only a necessary amount of sample is aspirated from the pipette, and this sample is discharged into a reaction vessel. This method is simple in structure, but poor in precision. It is particularly a problem when handling viscous samples such as blood. In the blood cell counting apparatus, therefore, the specimen is sampled by pushing out the specimen in cylindrical shape and removing it quantitatively by means of a sampling valve.

Figure 1:
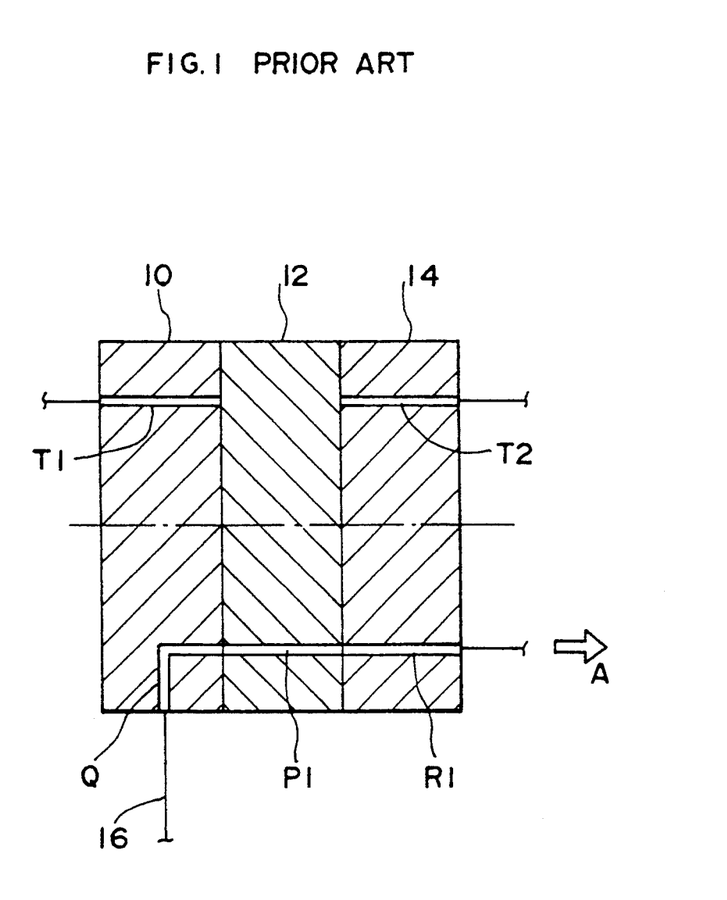
FIG. 1 is a sectional explanatory diagram showing the first state of a general conventional sampling valve with metering passages to be filled with sample.
Figure 2:
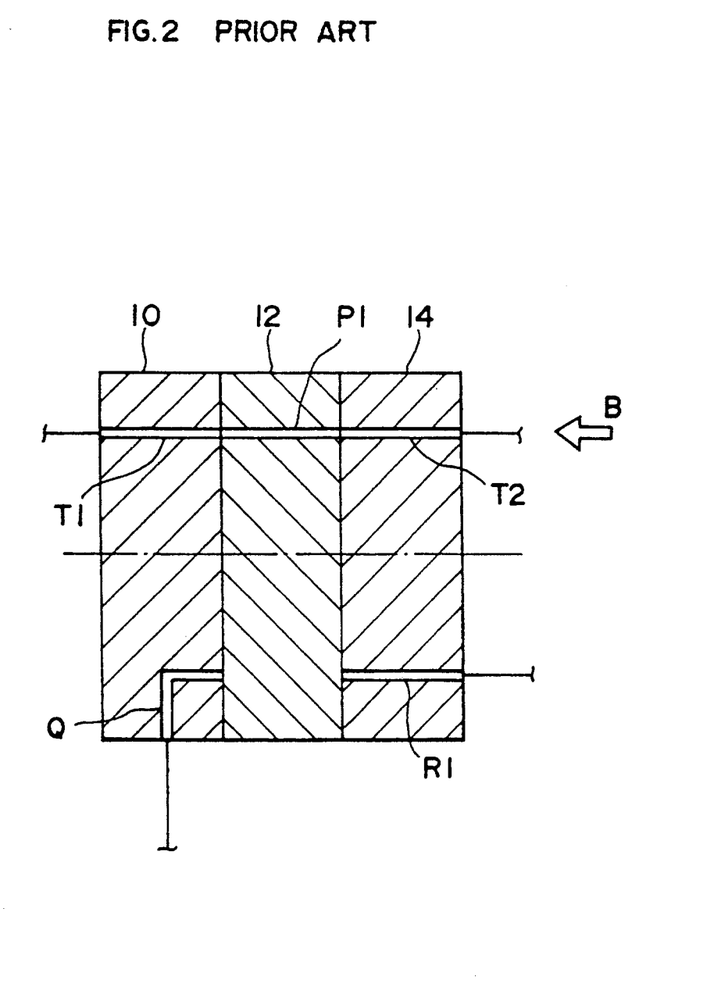
FIG. 2 is a sectional explanatory diagram showing the second state of a general conventional sampling valve with passages arranged for pushing out and transferring sample.

Referring now to FIG. 1 and FIG. 2, the construction and operation of a general sampling valve are explained briefly below. Usually, the sampling valve comprises two fixed elements 10, 14 and a movable element 12 held between the two fixed elements 10, 14. FIG. 1 and FIG. 2 show two states of the sampling valve. In FIG. 1, the sample flows in the direction of arrow A, that is, from a pipette 16 through a flow-in passage Q, a metering (measuring quantity) passage P1, and a flow-out passage R1, and fills up the metering passage P1 of the movable element 12 (which is called the first state). As the movable element 12 moves from the first state, it is changed to the state of FIG. 2 (which is called the second state), and the sample which filled up the metering passage P1 in the first state is pushed out, and is transferred outside the sampling valve, together with liquid such as a diluent, in the direction of arrow B from passage T2 to passage T1.

In the apparatus for analyzing specimen by sampling the specimen by means of a sampling valve, there has been a keen desire for realizing the discrete test (sampling only a necessary portion for each specimen, and analyzing).

OBJECT AND SUMMARY OF THE INVENTION

It is therefore a primary object of the present invention to provide an apparatus for analyzing liquid specimen capable of selecting only a necessary sample for measurement in each specimen, and treating such as diluting.

To achieve the above object, the present invention provides an apparatus for analyzing liquid specimen comprising a sampling valve which consists of two fixed elements in a stationary state, and a movable element held and movable between these fixed elements, having plural sample metering passages corresponding to plural measuring items disposed in the movable element, and plural passages to be connected as specified with the passages of the movable element disposed in the fixed elements, with the movable element moving while contacting the surface of the fixed elements, thereby establishing a first state during which the passages of the movable element are filled with sample, and a second state during which state the cylindrically shaped sample filling the passages is pushed out and transferring to other parts, aspiration means for feeding the sample into the sampling valve, plural dispensing means for supplying the liquid for dilution (diluent) to passages of the movable element, and plural chambers for receiving the samples pushed out by the liquid for dilution, which further comprises setting means for setting items to be measured, control means for generating a control signal for selectively actuating the dispensing means according to information from the setting means, and driving means receiving the control signal and driving the dispensing means, wherein when a specimen to be measured is set to measure a certain item, whether in the first state or in the second state, the dispensing means corresponding to that item is actuated, and when set not to measure that item, Whether in the first state or in the second state, the dispensing means corresponding to that item is not actuated.

In the above apparatus for analyzing liquid specimen, when non-measurement of a certain item occurs continuously by a specified number of times, although that specimen is not intended to measure that item, it is desired to control the dispensing means corresponding to the item so as to be actuated in the first state. When actuating the dispensing means, it is operated twice in the first state, and controlled so that the first dispensing liquid may be discharged from the chamber, while the second dispensing liquid may be held in the chamber.

In the above apparatus for analyzing liquid specimen, when a certain specimen is measured of a certain item, in the measurement of a next specimen, whether the specimen is to be measured of the same item or not, the dispensing means is operated twice in the first state, and controlled so that the first dispensing liquid may be discharged from the chamber, while the second dispensing liquid may be held in the chamber.

In the above apparatus for analyzing liquid specimen, the setting means preferably comprises means for presetting measuring items for each specimen on plural specimens, for example, work load setting means; or the setting means may preferably comprise setting means corresponding to measuring items, such as switch means.

In a practical example of the sampling valve, the movable element comprises metering passages, either one of the fixed elements comprises relay passages for connecting the metering passages in series in the first state, a flow-in passage communicating with the metering passage at the beginning of the series of passages connected in series in the first state for leading in the specimen to be analyzed from outside, and a flow-out passage communicating with the metering passage at the tail end of the series of passages connected in series in the first state for sending out the specimen to be analyzed to the outside, one fixed element comprises first transfer passages for communicating respectively with the metering passages in the second state, the other fixed element comprises second transfer passages for communicating respectively with the metering passages in the second state, the movable element comprises cleaning passages for communicating respectively with the passages in the first state, the aspiration means (for example, syringe) is connected to the flow-out passage, the dispensing means (for example, syringes) for analyzing the liquid for dilution (diluent) are respectively connected with the transfer passages of either the first or second transfer passages, and the chambers for receiving the sample pushed out by the liquid for dilution are respectively connected with the other transfer passages of the first or second transfer passages.

In the first state of the sampling valve, as the aspiration means is actuated, the sample flows in a series of series passages comprising the flow-in passage metering passages, relay passages, and flow-out passage; and each passage is filled up. At the same time, when a certain dispensing means is placed in operation, the dilution liquid (diluent) is sent into the chamber through the passages. This dilution liquid is used for cleaning.

Consequently, the sampling valve changes from the first state to the second state. As the dispensing means operates, the dilution liquid pushes out the sample measured quantitatively in the passage through the passages, and the dilution liquid and sample are mixed in the chamber, and the diluted specimen for measurement (examination) is prepared. The prepared diluted specimen is supplied into the measuring (examination) unit of the apparatus for analyzing liquid specimen, and is measured and analyzed.

Afterwards, the sampling valve returns to the first state again, and the liquid for cleaning (or diluent liquid) is supplied in the flow-out passage, and the sample remaining in the series of series passages is washed out, and the passages are cleaned.

DETAILED DESCRIPTION OF THE PREFERRED EMBODIMENTS

Referring now to the drawings, some of the preferred embodiments of the present invention are described in detail below.

Figure 3:
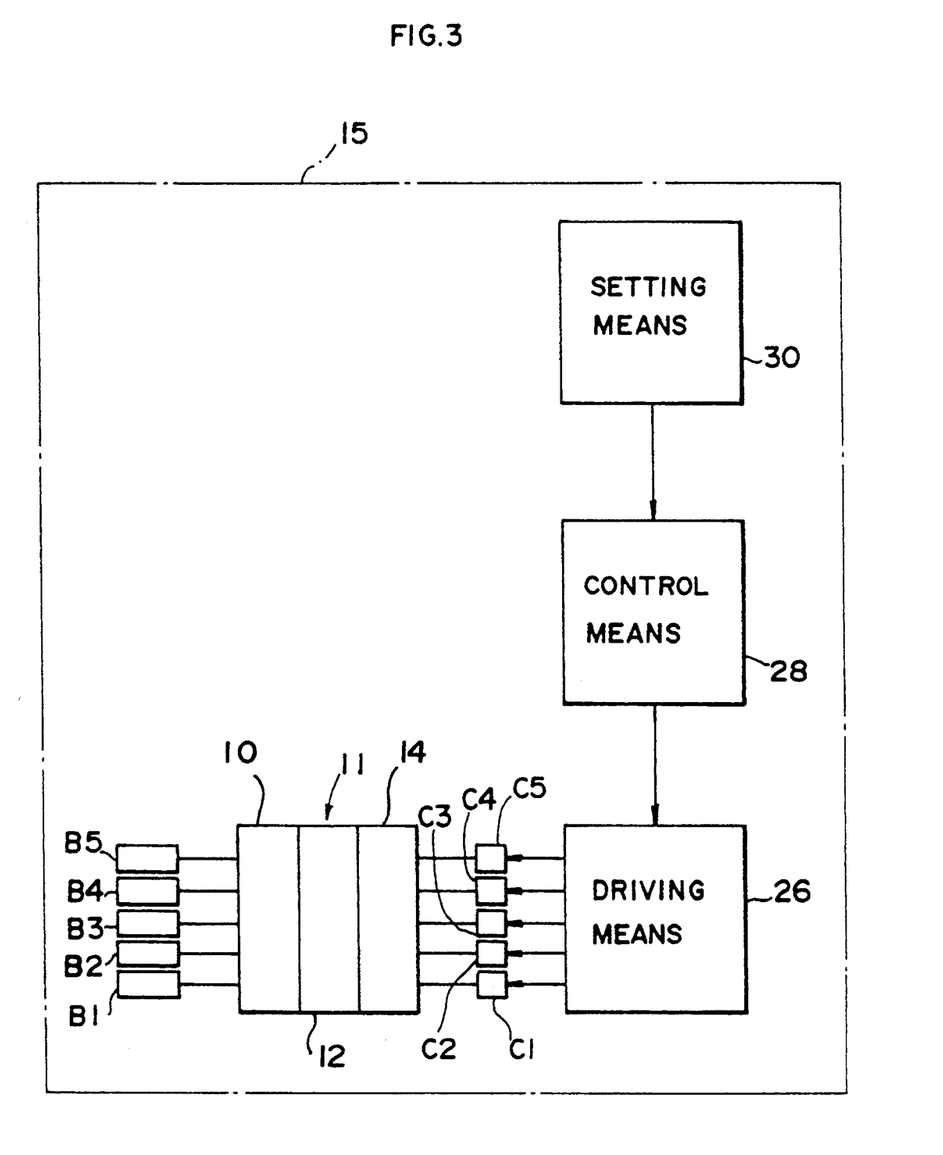
FIG. 3 is a schematic structural block drawing showing an embodiment of essential parts of an apparatus for analyzing liquid specimen according to the present invention.
Figure 4:
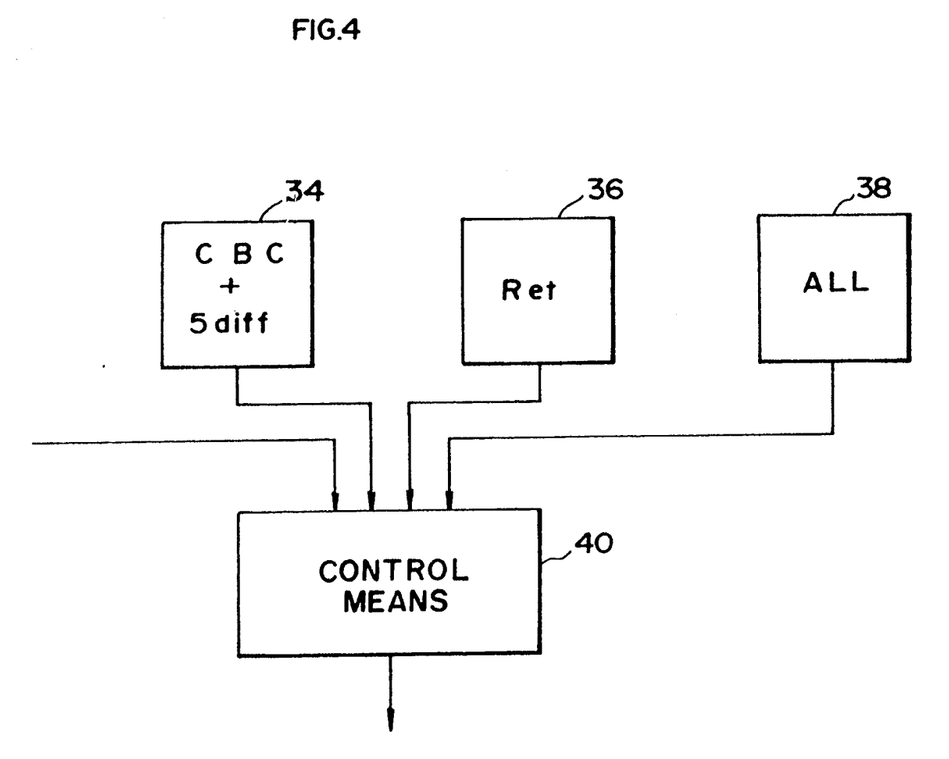
FIG. 4 is a schematic structural block drawing showing an example of the setting means in FIG. 3.
Figure 5:
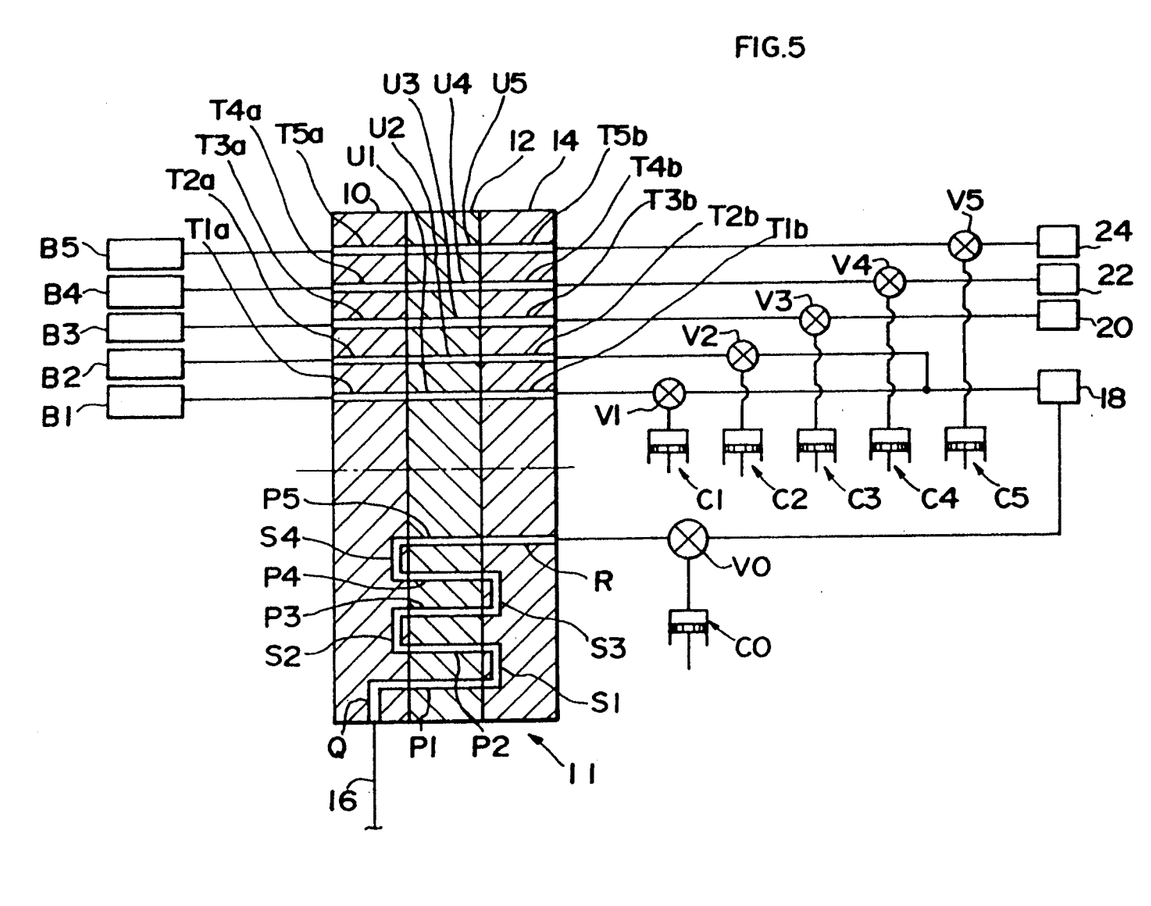
FIG. 5 is a sectional explanatory diagram showing the first state for filling the metering passages with sample in the sampling valve in FIG. 3.
Figure 6:
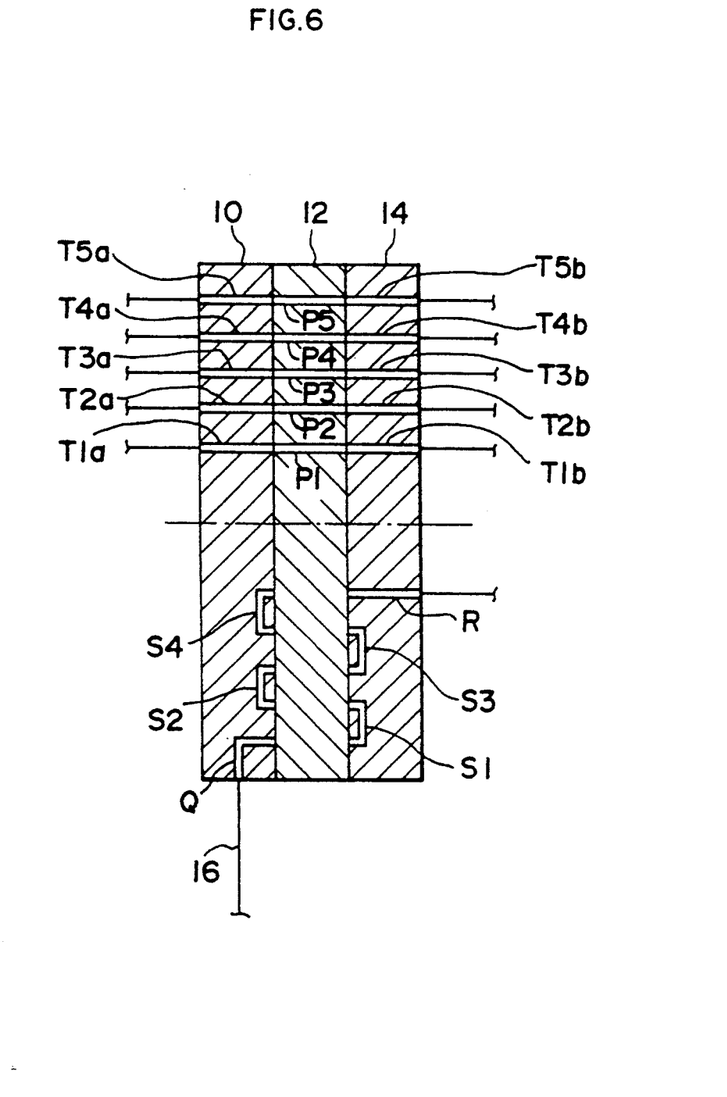
FIG. 6 is a sectional explanatory diagram showing the second state of the sampling valve of FIG. 3 for pushing out and transferring sample.

In FIG. 3 through FIG. 6, the present invention is shown as comprising an apparatus 15 for analyzing liquid specimen including a sampling valve 11 which consists of two fixed elements 10, 14 in a stationary state, and a movable element 12 held and movable between these fixed elements. The movable element 12 has plural sample metering passages $P_i$; $i=1, 2, \ldots$, corresponding to plural measuring items or characteristics to be measured disposed therein, and plural passages to be connected as specified with the passages $P_i$ disposed in the fixed elements 10, 14, with the movable element 12 moving while contacting the surface of the fixed elements 10, 14. FIG. 5 shows the first state of the sampling valve 11 during which the passages $P_i$ of the movable element 12 are filled with sample, and FIG. 6 shows the second state of the sampling valve 11 during which the sample filling the passages $P_i$ in a cylindrical shape are pushed out of the passages $P_i$ for transfer to other parts, the apparatus also comprises aspiration means CO (FIG. 5) for feeding sample into the sampling valve 11, and plural dispensing means $C_i$; $i=1, 2, \ldots$ for supplying the liquid for dilution to the passages $P_i$.

In addition, the apparatus also comprises plural chambers $B_i$; $i=1, 2, \ldots$ for receiving the samples pushed out by the liquid for dilution, setting means 30 for setting items to be measured, control means 28 for generating a control signal for selectively actuating the dispensing means $C_i$ according to the information from the setting means 30, and driving means 26 for driving the dispensing means $C_i$ by receiving the control signal.

When a specimen to be measured is set to measure a certain item, whether in the first state or in the second state, the dispensing means $C_i$ corresponding to that item is actuated, and when set not to measure that item, whether in the first state or in the second state, the dispensing means $C_i$ corresponding to that item is not actuated.

In the above apparatus for analyzing liquid specimen, when non-measurement of a certain item occurs continuously for a specified number of times, although that specimen is not intended to measure that item, it is desired to control the dispensing means $C_i$ corresponding to the item so as to be actuated in the first state. In the apparatus for analyzing liquid specimen, when actuating the dispensing means $C_i$, it is operated twice in the first state, and it is desired to be controlled so that the first dispensing liquid may be discharged from the chamber $B_i$, while the second dispensing liquid may be held in the chamber $B_i$.

In the apparatus for analyzing liquid specimen, when a certain specimen is measured of a certain item, in the measurement of a next specimen, whether the specimen is to be measured of the same item or not, the dispensing means $C_i$ is operated twice in the first state, and it is desired to be controlled so that the first dispensing liquid may be discharged from the chamber $B_i$, while the second dispensing liquid may be held in the chamber $B_i$.

In the apparatus for analyzing liquid specimen, the setting means 30 is preferably means for presetting measuring items for each specimen on plural specimens, for example, work load setting means, or the setting means 30 may be preferably setting means provided corresponding to measuring items, such as switch means.

In a practical example of the sampling valve 11, the movable element 12 comprises metering passages P1, P2, ..., Pn, either one of the fixed elements comprises relay passages S1, S2, ..., Sn-1 for connecting the metering passages P1, P2, ..., Pn in series in the first state, a flow-in passage Q communicates with the metering passage P1 at the beginning of the series of passages connected in series in the first state for leading in specimen to be analyzed from outside, and a flow-out passage R communicates with the metering passage Pn at the tail end of the series of passages connected in series in the first state for sending out the specimen to be analyzed outside of the sampling valve 11, one of the fixed elements includes first transfer passages T1a, T2a, ..., Tna for communicating respectively with the metering passages P1, P2, ..., Pn in the second state (FIG. 6), the other of the fixed elements includes second transfer passages T1b, T2b, ..., Tnb for communicating respectively with the metering passages P1, P2, ..., Pn in the second state, the movable element 12 includes cleaning passages U1, U2, ..., Un for communicating respectively with the passages T1a and T1b, T2a and T2b, ..., Tna and Tnb in the first state, the aspiration means (for example, a syringe) CO is connected to the flow-out passage R, the dispensing means (for example, syringes) C1, C2, ..., Cn for analyzing the liquid for dilution are respectively connected with the transfer passages T1b, T2b, ..., Tnb of either the first or second transfer passages, and the chambers B1, B2, ..., Bn for receiving the sample pushed out by the liquid for dilution are respectively connected with the other transfer passages T1a, T2a, ..., Tna of the first or second transfer passages.

In the first state of the sampling valve 11, as the aspiration means CO is actuated, sample flows in a series of series passages comprising the flow-in passage Q, metering passages P1, ..., relay passages S1, ..., flow-out passage R, and as a result each passage is filled up. At the same time, when a certain dispensing means Ci is placed in operation, the dilution liquid is sent into the chamber Bi through the passages Tib, Ui, Tia. This dilution liquid is used for cleaning.

Subsequently, the sampling valve 11 changes from the first state to the second state. As the dispensing means Ci operates, the dilution liquid pushes out the sample measured quantitatively in the passage Pi through the passages Tib, Pi, Tia, and the dilution liquid and sample are mixed in the chamber Bi, and the diluted specimen for measurement is prepared. The prepared diluted specimen is supplied into a measuring unit (not shown) of the apparatus 15 for analyzing liquid specimen, and is measured and analyzed.

Afterwards, the sampling valve 11 returns to the first state again, and the liquid for cleaning (or diluent liquid) is supplied in the flow-out passage R, and the sample remaining in the series of series passages is washed out, and the passages are cleaned.

In the apparatus for analyzing liquid specimen of the present invention, measuring items of specimens may be set by the setting means 30. To set the items, for example, as shown in the work load list in the work load setting means in Table 1 shown hereinafter, by entering the specimen number information in the work load setting means, and the item selection information of either "1" (to measure) or "0" (not to measure) in each measuring item, items may be present for plural specimens to be measured. This is useful when automatically feeding the specimens by a sampler (sample feeding device). Besides, as shown, for example, in FIG. 4, by selecting the measuring item by the switch means, the measuring items may be changed. This is useful for manual measurement.

According to the data of measuring items set in this way by the setting means 30, the control means 28 generates a control signal for actuating the dispensing means as specified. According to this control signal, the driving means 26 drives each dispensing means.

When not measuring a certain item, it is not necessary to prepare a diluted specimen for measuring that item. Hence, the driving means is controlled not to operate the dispensing means Ci corresponding to that item.

When the passages Pi are aligned with the passages Tia, Tib in the second state, specimen in passage Pi is slightly mixed into the passages Tia, Tib gradually. It is therefore desirable to introduce a cleaning operation before the specimen mixture is progressed. More practically, when measurement of a certain item is not executed continuously for a specified number of times, that is, when the dispensing means Ci does not operate continuously for a specified number of times, although that item is not measured, the dispensing means Ci is operated in the first state to clean the passages Tia, Tib.

At this time, the dispensing means Ci may be operated twice in the first state, so that a first dispensing liquid is discharged from the chamber Bi and a second dispensing liquid is held in the chamber Bi. In this case, the liquid dispensed into the chamber Bi the second time is a liquid free of sample (the diluent liquid itself), and therefore the chamber Bi is effectively not contaminated.

When a certain item is measured for a certain specimen, then in the measurement of the next specimen, whether that item is measured or not, the dispensing means Ci may be operated twice in the first state, so that a first dispensing liquid is discharged from the chamber Bi and a second dispensing liquid is held in the chamber Bi. In this case, since the chamber Bi is immediately cleaned, it is also effective not to contaminate the chamber Bi.

FIG. 3 is a schematic diagram of an embodiment of essential parts of an apparatus for analyzing liquid specimen (for example, blood cell counter) of the present invention. FIG. 4 is a diagram showing a practical example of the setting means 30. FIGS. 5, 6 are diagrams showing a fluid circuit around the sampling valve 11 in FIG. 3. More specifically, FIG. 5 shows the first state of the sampling valve 11, and FIG. 6 shows its second state. In FIG. 6, the dispensing means, chambers and others are omitted for the sake of simplicity of illustration.

In this embodiment, the sampling valve 11 is provided with, for example, five metering passages P1, P2, P3, P4, P5. Accordingly, five first and second transfer passages, and cleaning passages are provided, that is, T1a, T2a, T3a, T4a, T5a (first transfer passages), T1b, T2b, T3b, T4b, T5b (second transfer passages), and U1, U2, U3, U4, U5 (cleaning passages), and five dispensing means (for example, syringes) and chambers are also provided, that is, C1, C2, C3, C4, C5 (dispensing means), and B1, B2, B3, B4, B5 (chambers). There are four relay passages S1, S2, S3, S4 for connecting the metering passages P1, P2, P3, P4, P5 in series. Numeral 16 is a pipette, 18, 20, 22, 24 are cleaning liquid (diluent liquid) tanks, and V0, V1, V2, V3, V4, V5 are three-way valves. The diluent liquid may be also used as the cleaning liquid.

Of the metering passages, the passages P1, P2, P3 determine the specimens for measuring eight items of CBC (complete blood count), i.e., ordinary blood counting items. These are: WBC (white blood cells), RBC (red blood cells), HGB (hemoglobin), HCT (hematocrit), MCV (mean red corpuscular volume), MCH (mean red corpuscular hemoglobin), MCHC (mean red corpuscular hemoglobin concentration), and PLT (platelets). The passage P4 determines the quantity of the specimens for measuring WBC 5diff (five classifications of leukocytes). The passage P5 determines the quantity of the specimens for measuring Ret (reticulocytes).

Hence, in the case of a CBC measurement, the group of dispensing means C1, C2, C3 is actuated, in the case of a WBC 5diff measurement, the dispensing means C4 operates, and in the case of an Ret measurement, the dispensing means C5 is actuated, and in this embodiment, since there are four measuring patterns 1. measurement of CBC only (hereinafter item 1)
2. measurement of CBC+WBC 5diff (item 2)
3. measurement of Ret only (item 3)
4. measurement of CBC+WBC 5diff+Ret, that is, ALL (item 4), the dispensing means may be operated in a group of
C1, C2, C3 for item 1
C1, C2, C3, C4 for item 2
C5 for item 3, and
C1, C2, C3, C4, C5 for item 4.

Table 1 is an example of a work load list for the work load setting means for setting items 1 to 4. Items are set for the specimens before the specimens are measured by entering the ID No. (specimen identification number) (an arbitrary number of up to eight digits), and entering for each item ("1" if measurement is to occur, or "0" if measurement is not to occur. According to the information set in the work load setting means, it is judged which group of dispensing means out of the setting items 1 to 4 should be actuated by the control means 28, and a specified control signal is generated at the specified time in the measurement sequence. According to the control signal, the driving means 26 drives the appropriate dispensing means. This setting by the work load setting means is useful in automatic measurement by using a sampler.

TABLE 1

| ID No. | CBC | WBC 5diff | Ret |
|---|---|---|---|
| 1001 | 1 | 0 | 0 |
| 1002 | 1 | 1 | 0 |
| 1003 | 0 | 0 | 1 |
| 1004 | 1 | 1 | 1 |

FIG. 4 shows another example of setting means. Numerals 32, 34, 36, 38 are switches, and the switch on/off information is entered in the control means 40, and one of the items 1 to 4 is judged. When the specimen is later measured, the dispensing means is actuated at a specific timing, and the item set by the switch is measured. By changing the switch setting, the measuring item may be selected for each specimen. Such setting by the switch is useful in manual measurement.

It is extremely useful when the blood cell counter is provided with both setting means. Either one of the two setting means may be selected depending on the sampler mode or manual mode. By pressing the start switch for the sampler mode, the sampler begins to work. By pressing the start switch for the manual mode, the sample is aspirated.

In the case of the manual mode, by selecting the four switches 32, 34, 36, 38 provided in the main body of the apparatus for analyzing liquid specimen before measurement, the measuring items may be set or changed. Since the same setting is maintained until the setting is changed, when measuring the same measuring item, it is not necessary to set every time when measuring. After setting of the measuring item, the manual start switch is pressed to aspirate the specimen.

In the case of the sampler mode, every specimen number (ID No.) can be set by the work load setting means (personal computer) connected to the apparatus for analyzing liquid specimen. When only the specimen number is set, the error is displayed, and if the start switch for the sampler mode is pressed, the sampler does not start. Or, if necessary, it may be also possible to set to judge when all items are measured. In this way, after preparing the work load list, the rack holding the specimens is installed on the sampler, and the information of specimen numbers and measuring items is transferred to the control means 30 of the apparatus for analyzing liquid specimen by the start switch of the work load setting means, thereby Starting the operation of the sampler.

In the embodiment, when non-measurement of a certain item occurs continuously for a specified number of times, although the specimen is not to be measured of that item, the dispensing means Ci corresponding to that item may be preferably designed to be actuated in the first state.

For example, when item 1 is to be measured continuously, the sample is determined quantitatively in the passages P1, P2, P3, P4, P5 of the sampling valve 11 as shown in FIG. 5. The specimens to be used for measurement are only specimens in the passages P1, P2, P3, while specimens in the passages P4, P5 are not used. That is, only the dispensing means C1, C2, C3 are operated in the first and second states of the sampling valve 11, while the dispensing means C4, C5 are not placed in action. However, the specimens in passages P4, P5 contact the passages T4a, T4b, T5a, T5b, and are very slightly mixed into the passages. If, for example, the dispensing means C4, C5 do not operate continuously for ten times, in the next measurement, the dispensing means C4, C5 are actuated, and the passages T4a, T4b, T5a, T5b are cleaned.

Being thus arranged, the present invention brings about the following effects.

(1) In the apparatus for analyzing liquid specimen having a sampling valve, it is possible to realize a so-called discrete test of analyzing by sampling only a necessary sample for each specimen. That is, according to the item setting information from the setting means, the dispensing means is selectively actuated, and therefore the diluted sample for measurement may be prepared by selecting only the portion necessary for measurement, so that the diluent liquid and others may be saved.

(2) When not measuring a certain item, the dispensing means Ci corresponding to that item is actuated as required, and the passages may be cleaned preventively by that dispensing liquid before progress of contamination, so that the risk of contamination may be eliminated.

Having described preferred embodiments of the present invention with reference to the accompanying drawings, it is to be understood that the present invention is not limited to those precise embodiments, and that various changes and modifications may be effected therein by one skilled in the art without departing from the scope or spirit of the present invention as defined in the appended claims.

What is claimed is:

1. An apparatus for analyzing liquid specimens, comprising: a sampling valve having two fixed elements in a stationary state, and a movable element held and movable between the fixed elements, said movable element having a plurality of sample metering passages (Pi; i=1, 2, ... ) corresponding to a plurality of measuring items disposed therein, and said fixed elements each having a plurality of passages to be connected with the passages (Pi) of said movable element, with the movable element moving while contacting the surface of the fixed elements, thereby defining a first state of the sampling valve during which the passages (Pi) of the movable element are filled with sample, and a second state of the sampling valve during which sample is pushed out of the passages (Pi) in a cylindrical shape and transferred to other parts;

aspiration means (CO) for feeding sample into the sampling valve;

a plurality of dispensing means (Ci; i=1, 2, ... ) for supplying the liquid for dilution to the passages (Pi) of the movable element;

a plurality of chambers (Bi; i=1, 2, ... ) for receiving the samples pushed out by the liquid for dilution;

setting means for setting items to be measured;

control means for generating a control signal for selectively actuating the dispensing means (Ci) according to the information from the setting means; and driving means for receiving the control signal and driving the dispensing means (Ci), wherein the dispensing means (Ci) corresponding to an item of a specimen to be measured is actuated when the specimen to be measured is set to measure that item, and is not actuated when a specimen is not set to measure that item, and wherein when nonmeasurement of a certain item occurs continuously for a specified number of times, the dispensing means (Ci) corresponding to that item to be measured is controlled to be actuated in the first state.

2. An apparatus for analyzing liquid specimens according to claim 1, further wherein when a certain item is measured of a certain specimen, in the measurement of a next specimen, whether the certain item of the next specimen is to be measured or not, the dispensing means (Ci) is operated twice in the first state, and is controlled to discharge the first dispensing liquid from the chamber (Bi), and to keep the second dispensing liquid in the chamber (Bi).

3. An apparatus for analyzing liquid specimens according to claim 1, further wherein when actuating the dispensing means (Ci), it is operated twice in the first state, and is controlled to discharge the first dispensing liquid from the chamber (Bi) and to keep the second dispensing liquid in the chamber (Bi).

4. An apparatus for analyzing liquid specimens according to claim 1, further wherein when a certain item of a certain specimen is measured, in the measurement of the next specimen, whether the specimen is to be measured of that item or not, the dispensing means (Ci) is operated twice in the first state, and is controlled to discharge the first dispensing liquid from the chamber (Bi), and to keep the second dispensing liquid in the chamber (Bi).

5. An apparatus for analyzing liquid specimens according to claim 1, further wherein the setting means comprises means for presetting the measuring items for every specimen of a plurality of specimens.

6. An apparatus for analyzing liquid specimens according to claim 1, further wherein the setting means is the setting means provided corresponding to the measuring item.

* * * * *